(12) United States Patent
North, Jr.

(10) Patent No.: US 6,387,277 B1
(45) Date of Patent: May 14, 2002

(54) METHOD FOR REMOVING CONTAMINANTS FROM A FLUID STREAM

(76) Inventor: Howard L. North, Jr., P.O. Box 390, Oldwick, NJ (US) 08858-0390

( * ) Notice: Subject to any disclaimer, the term of this patent is extended or adjusted under 35 U.S.C. 154(b) by 0 days.

(21) Appl. No.: 09/695,013

(22) Filed: Oct. 24, 2000

Related U.S. Application Data

(63) Continuation of application No. 09/401,463, filed on Sep. 22, 1999, now Pat. No. 6,302,836.
(60) Provisional application No. 06/102,698, filed on Oct. 1, 1998.

(51) Int. Cl.$^7$ .......................... G01N 21/00; B04B 11/00
(52) U.S. Cl. .................. 210/745; 210/739; 210/782; 210/787; 210/800; 210/803; 422/72; 422/82.05; 422/82.09; 422/101; 422/102; 422/103; 494/10; 494/37
(58) Field of Search ................................ 210/739, 745, 210/781, 782, 787, 800, 803, 94, 97, 416.1, 424; 422/72, 82.05, 82.09, 101, 102, 103; 494/10, 16, 19, 37

(56) References Cited

U.S. PATENT DOCUMENTS 4,828,716 A * 5/1989 McEwen et al. ............ 210/745
5,308,506 A * 5/1994 McEwen et al. ............ 210/745

* cited by examiner

Primary Examiner—David A. Reifsnyder

(57) ABSTRACT

An ordinary vacuum blood collection tube assembly is rotated about its longitudinal axis to partition a blood sample into serum and formed elements by centrifugation. While still rotating a higher density, immiscible, inert liquid is pumped into the vacuum blood collection tube assembly thereby displacing the lower density serum towards the axis of rotation and thence out of the vacuum blood collection tube assembly to a serum receiver vessel. A contaminant detector located on the serum delivery conduit controls a 3 way valve to divert contaminants from the removed serum to a waste vessel so only clean serum is delivered to the serum receiver vessel. The serum delivery conduits, serum cannula, contaminant detector, and diverter valve are washed and dried between successive samples to limit sample carryover effects to acceptably low levels. These operations may be fully automated so a carousel of blood samples may be processed sequentially to deliver clean serum to a second carousel of serum cups without operator intervention at a rate of about one sample per minute.

7 Claims, 7 Drawing Sheets

METHOD FOR REMOVING CONTAMINANTS FROM A FLUID STREAM

Figure 1:
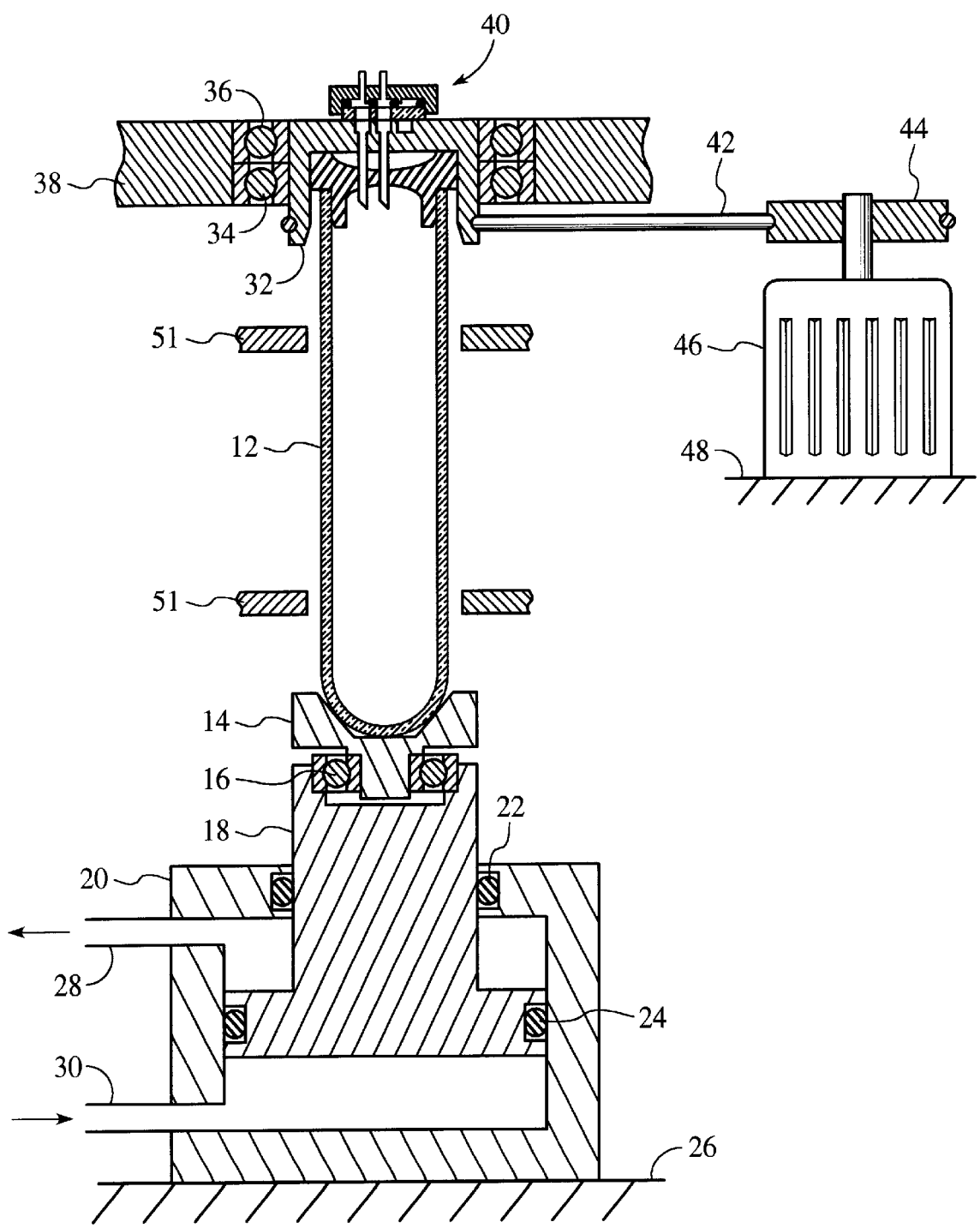

This application is a divisional of U.S. application Ser. No. 09/401,463 filed Sep. 22, 1999, now U.S. Pat. No. 6,302,836 which claims the benefit of U.S. Provisional Application No. 06/102,698 filed Oct. 1, 1998.

BACKGROUND—FIELD OF INVENTION

This invention relates to a method for partitioning a blood sample and obtaining clean serum from an unopened vacuum blood collection tube assembly.

BACKGROUND—DESCRIPTION OF PRIOR ART

Hospital clinical laboratories often analyse blood serum for various chemical constituents by using automated analyzers. Blood is drawn from a patient into a vacuum blood collection tube assembly. After the blood clots this tube is placed in a centrifuge which causes the clot material to move to the end of the tube distal to the stopper. The less dense serum is then between the clot material and the stopper.

Serum is then removed from the tube and presented by various methods to a blood serum chemistry analyzer. One method requires removal of the stopper and removal of serum by pipetting or decanting serum into a serum cup from which serum is dispensed to an analyzer. These operations may be automatic or manual or a mixture of these methods.

Serum may be removed from an unopened vacuum blood collection tube assembly following centrifugation without removal of the stopper by piercing the elastomeric stopper with a cannula so the distal end of the cannula is fully immersed in serum. Serum is then aspirated from the tube via the cannula by a syringe or pump and delivered to a serum cup or an analyzer. These operations may be manual or automatic or a mixture of these methods.

Various automated apparatus have been constructed to automate the operations of separating serum from the clot by centrifugation, removal of the stopper, and removing and dispensing of serum. Automation of centrifugal separation of serum and clot using conventional centrifuges has proven to be complex and costly due to the large number of separate operations required. These include the following:
(a) removing the blood tube from a carousel or rack
(b) placing the blood tube in a centrifuge rotor
(c) repeating (a) and (b) for a number of blood tubes
(d) balancing the centrifuge rotor
(e) closing the centrifuge lid
(f) rotating the centrifuge rotor for a predetermined time and speed sufficient to separate serum from the clot
(g) stopping the centrifuge rotor
(h) opening the centrifuge lid
(i) removing each tube from the centrifuge rotor
(j) placing each blood tube in a carousel or rack suitable for subsequent operations of serum removal and dispensing.

These operations have proven to be difficult to automate economically rendering this approach of limited value.

In an effort to more readily automate the centrifugation operation McEwen et al in U.S. Pat. No. 5,308,506 issued May 3, 1994 employ the method of rotating the vacuum blood collection tube assembly about its longitudinal axis. This method thus avoids most of the above (a) through (j) steps of conventional centrifugation. However, McEwen et al then employ a slidable piston positioned within the vacuum blood collection tube assembly during centrifugation to preserve the separation of serum and clot after rotation of the blood tube ceases. McEwen et al also use a special device shown on FIG. 8 of his patent to remove and dispense serum from an unopened vacuum blood collection tube assembly. Removal of serum from an unopened vacuum blood collection tube assembly is highly desireable since it avoids the generation of biohazardous aerosols sometimes generated by removal of the blood tube stopper, which have caused infection with HIV or hepatitis.

Mcwen et al invention suffers from the following shortcomings which have limited its utility:
1. It requires a special vacuum blood collection tube assembly containing a slidable piston which adds cost to the blood tube and adds to the laboratory stockroom more work and the need for more space.
2. It requires a special device to remove serum from an unopened vacuum blood collection tube assembly which adds cost to the process since the special device must either be disposable or must be washed after each use to avoid serum sample carryover problems.
3. It requires a special centrifuge apparatus to rotate the vacuum blood collection tube assembly about its longitudinal axis.
4. The operations of serum separation by centrifugation and removal followed by serum dispensing are all separate operations and are not integrated. They thus require manual interventions to move blood samples and serum samples from one apparatus to another and to dispense serum. These manual interventions lead to significant time and labor costs.
5. There is no provision for the removal from the dispensed serum contaminants such as air, microclots, cellular aggregations which can cause malfunction of automated serum chemistry analyzers.

OBJECTS AND ADVANTAGES

Accordingly, in addition to avoiding many of the shortcomings and disadvantages of U.S. Pat. No. 5,308,506, further objects and advantages of the present invention are:
(a) to provide a single apparatus operating by a method which fully automates and integrates the operations of separation of serum from clots, removal of serum from an unopened vacuum blood collection tube assembly, and dispensing of removed serum to a remote receiver vessel.
(b) to provide the operations of (a) above while using a standard, unmodified vacuum blood collection tube assembly without any special features such as an enclosed slidable piston
(c) to provide the operations of (a) above without use of any one time use or disposable devices
(d) to provide the operations of (a) above and delivering clean serum free from contaminants such as air, microclots, cellular aggregates, or fibrin strands
(e) to provide clean serum from an unopened vacuum blood collection tube assembly including the operations of separating serum from the clot, removing and cleaning serum, and dispensing cleansed serum in a period of time of about 1 minute.
(f) to provide the operations of (e) above with significantly less cost for labor and materials than conventional methods
(g) to provide the operations of (e) above without use of devices requiring disposal
(h) to provide for the washing and drying of reusable serum conduits to reduce sample carryover effects to acceptably low levels
(i) to provide means for dispensing a predetermined volume of clean serum from an unopened vacuum blood collection tube assembly to a remote receiver vessel Other objects and advantages will become apparent from a consideration of the ensuing description and drawings.

DRAWING FIGURES

Figure 2:
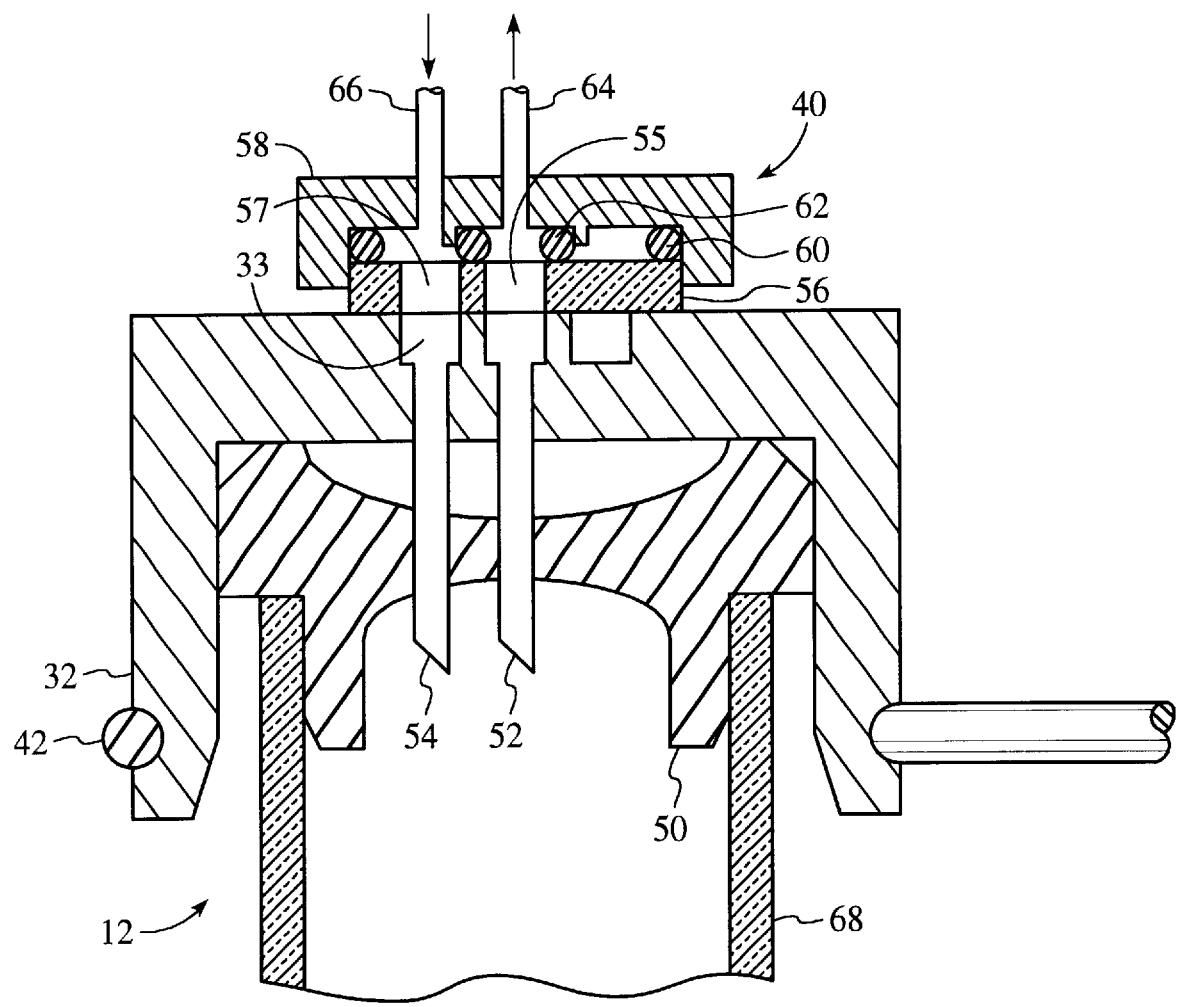
Figure 3:
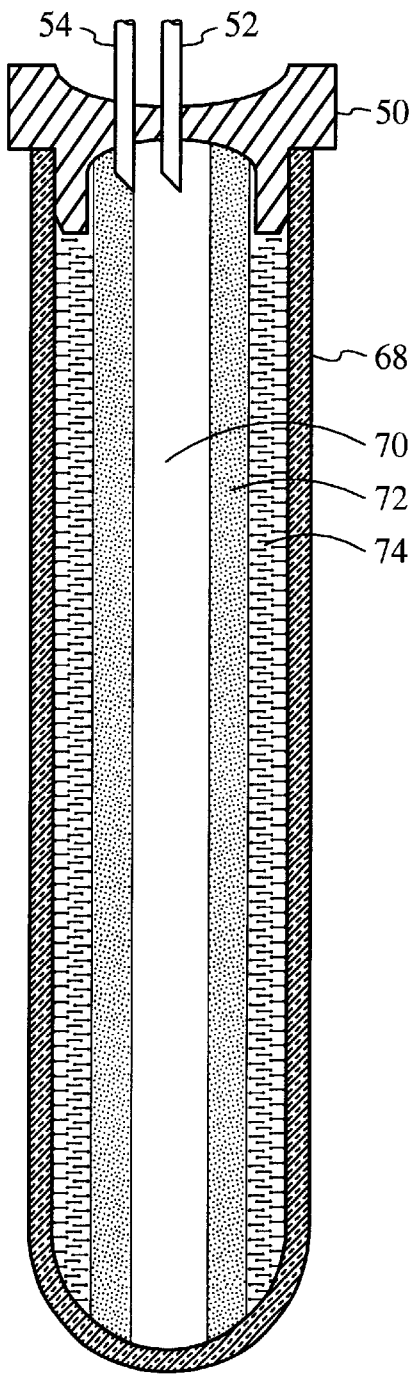
Figure 4:
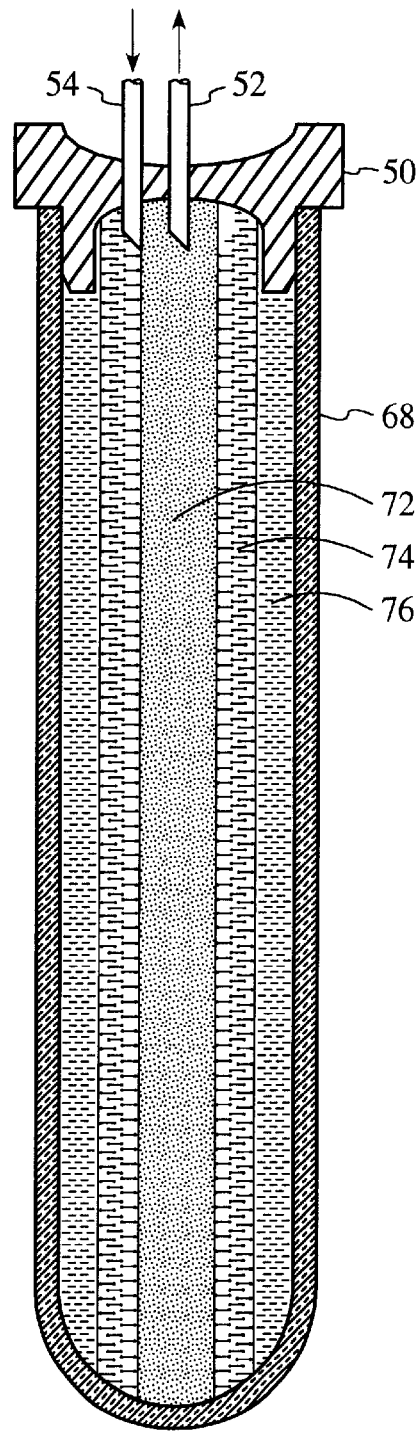
Figure 5:
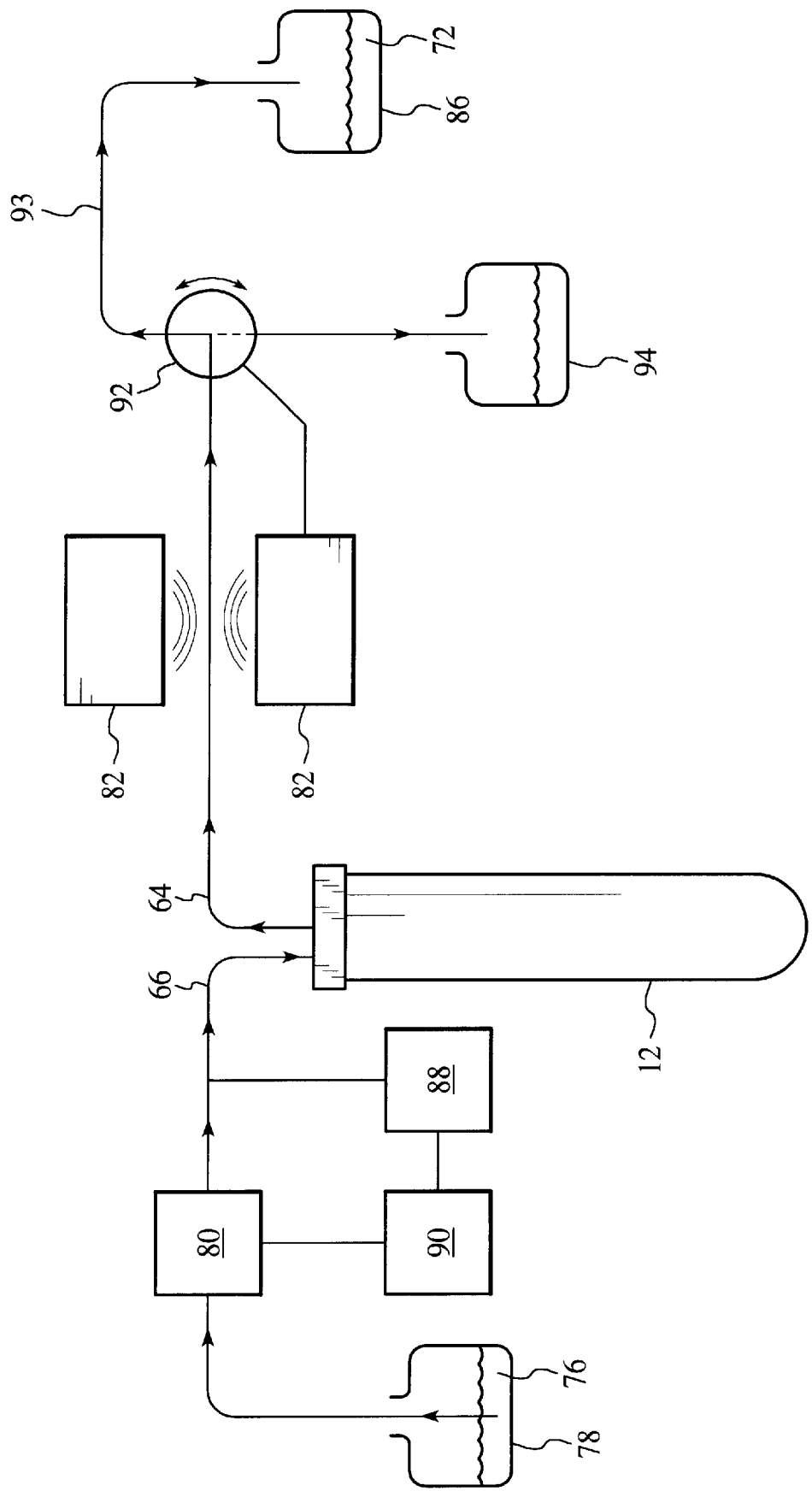
Figure 6:
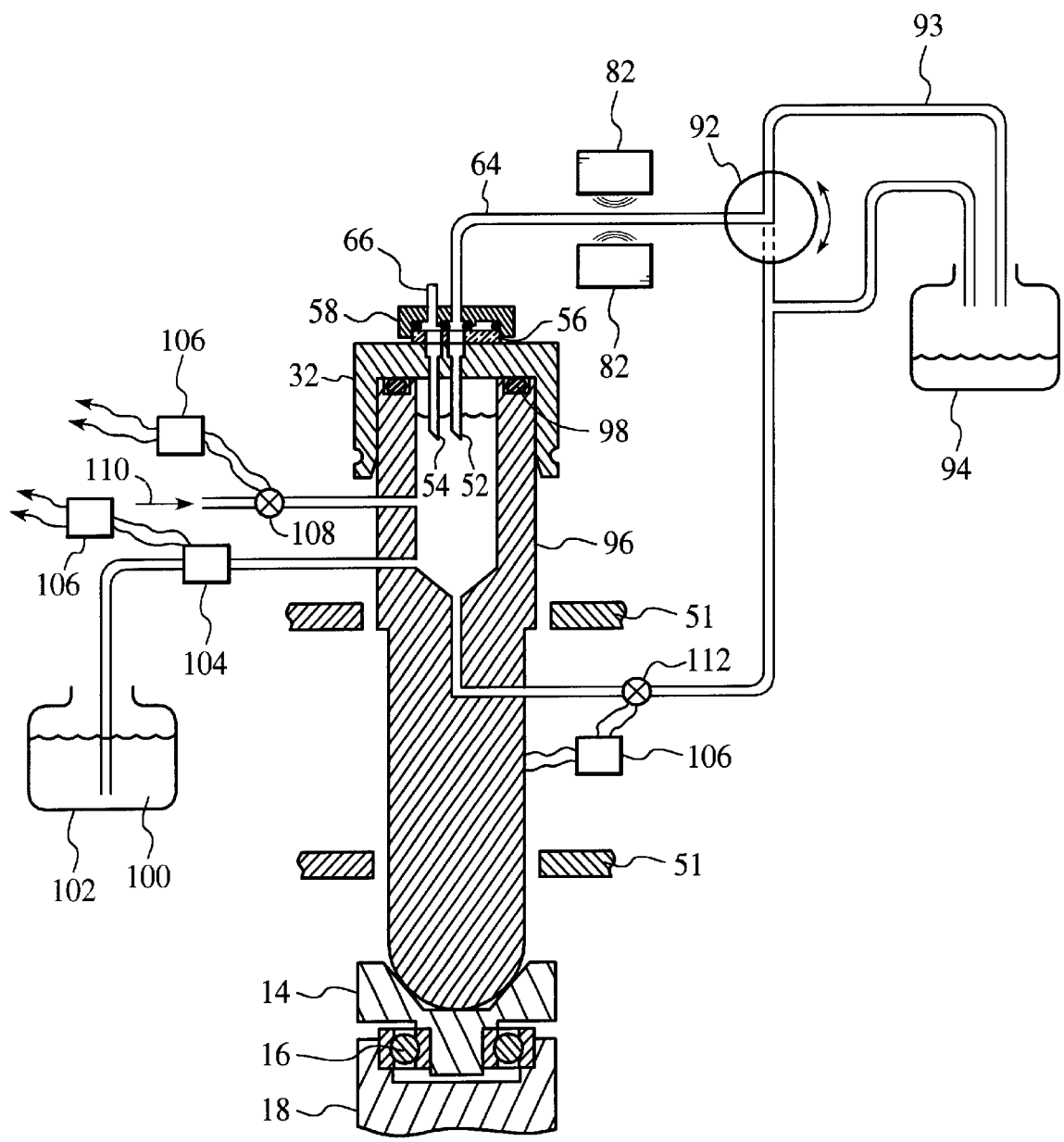
Figure 7:
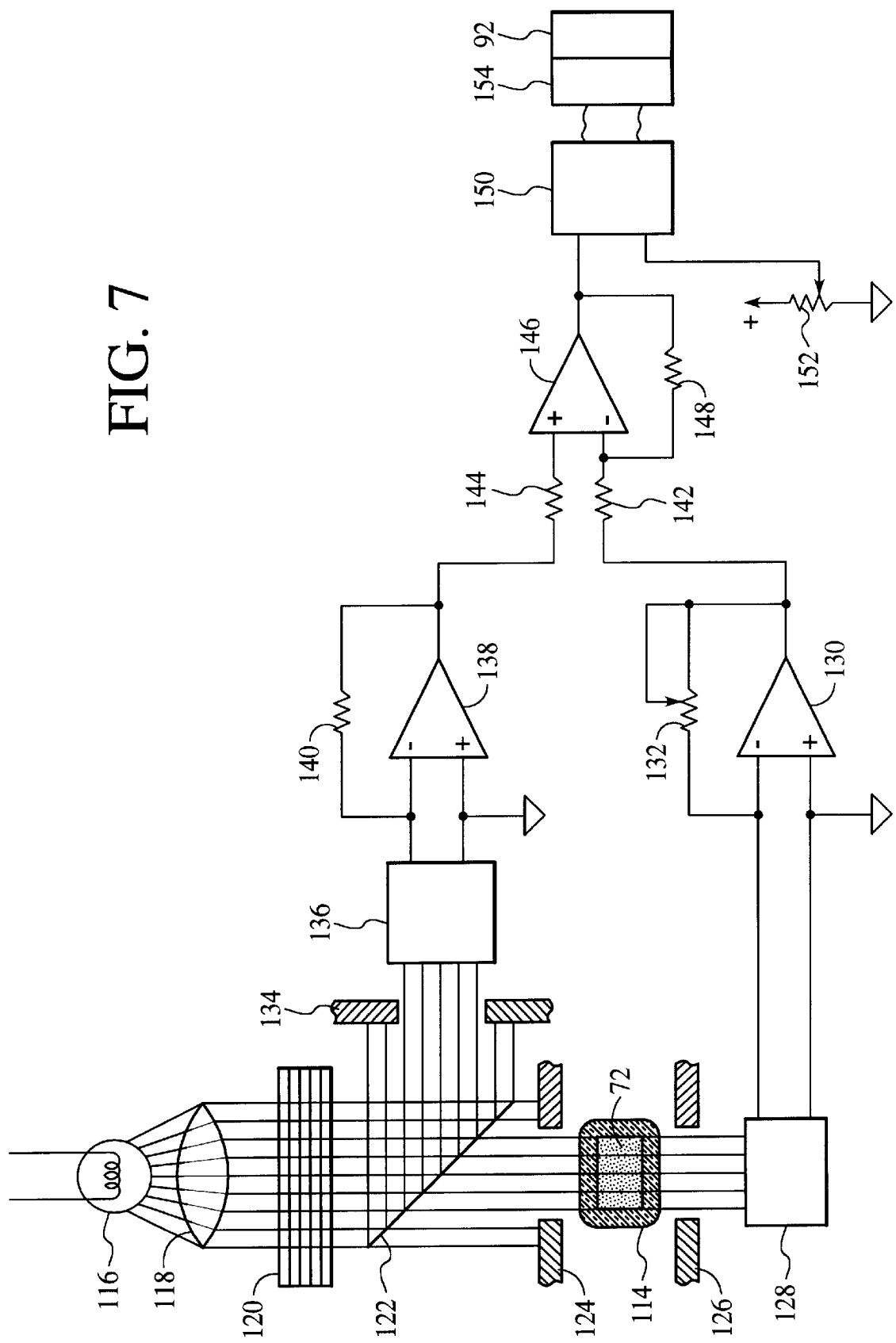
Figure 8:
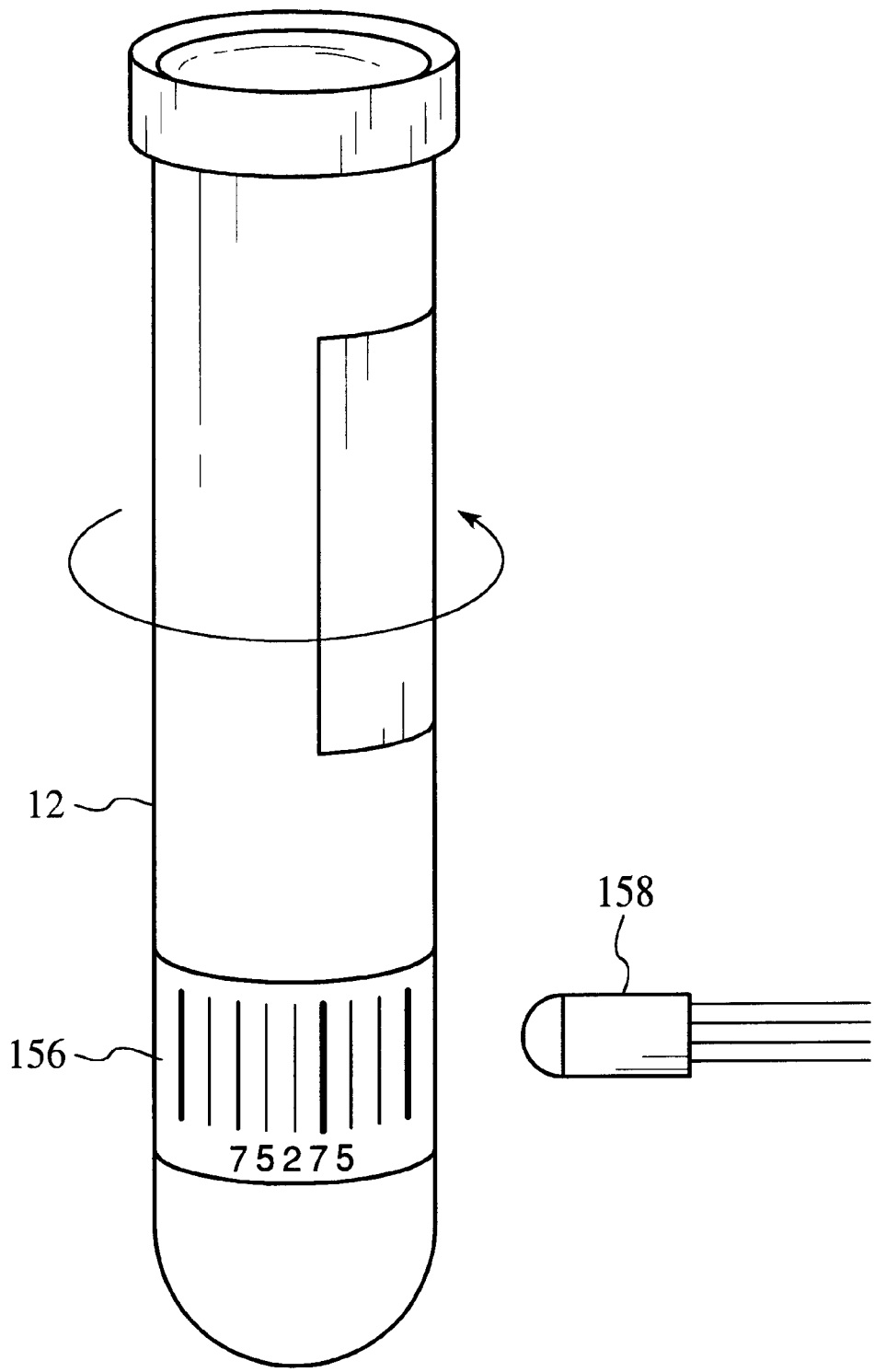

FIG. 1 shows a vacuum blood collection tube assembly, supports, and rotational drive FIG. 2 shows cannulae penetrating the stopper and a face seal FIG. 3 shows positions of serum and formed elements after centrifugation FIG. 4 shows positions of serum, formed elements, and inert fluid during serum expulsion FIG. 5 is a fluid schematic for serum expulsion FIG. 6 is a fluid schematic for washing and drying serum conduits FIG. 7 shows a contaminant detector and 3 way valve control schematic FIG. 8 shows a sample identification reader

REFERENCE NUMERALS IN DRAWINGS 12 vacuum blood collection tube assembly
14 tube support
16 bearing
18 piston
20 cylinder
22 seal
24 seal
26 stationary structure
28 port
30 port
32 stopper support
33 annular groove
34 bearing
36 bearing
38 stationary structure
40 face seal assembly
42 drive belt
44 pulley
46 motor
48 stationary structure
50 stopper
51 carousel
52 serum cannula
54 inert fluid cannula
55 hole
56 face seal
57 hole
58 face seal holder
60 O-ring
62 O-ring
64 serum conduit
66 inert fluid conduit
68 vacuum blood collection tube
70 air
72 serum
74 formed elements
76 inert fluid
78 inert fluid reservoir
80 pump
82 contaminant detector
86 serum receptacle
88 pressure switch
90 electronic control
92 3 way valve
93 serum delivery conduit
94 waste reservoir
96 washing tube
98 O-ring
100 washing fluid
102 washing fluid reservoir
104 pump
106 timer
108 normally closed valve
110 compressed air
112 normally closed valve
114 flow cell
116 lamp
118 lens
120 band pass filter
122 beam splitter
124 aperture
126 aperture
128 silicon PIN photodiode
130 operational amplifier
132 potentiometer
134 aperture
136 silicon PIN photodiode
138 operational amplifier
140 resistor
142 resistor
144 resistor
146 operational amplifier
148 resistor
150 pulse duration and time delay circuitry
152 potentiometer
154 electric actuator
156 machine readable markings
158 optical identification sensor

DESCRIPTION—FIGS. 1 THROUGH 8

Referring to FIG. 1 item 12 is a vacuum blood collection tube assembly containing a clotted blood sample and some residual air. Item 51 is a rotary carousel containing a plurality of tube assemblies. Item 14 is a tube support having a conical surface mating with item 12 and connected to a bearing 16 located in a piston 18 which slides in a cylinder 20 and is sealed thereto by seals 22 and 24. Cylinder 20 is supported by a stationary structure 26 and is connected to a conventional source of high and low fluid pressure (not shown) by ports 28 and 30. A stopper support 32 engages a stopper 50 and is connected by bearings 34 and 36 to a stationary structure 38. Stopper support 32 is rotated by motor 46, pulley 44, and drive belt 42 and is in contact with face seal assembly 40.

Referring to FIG. 2 a serum cannula 52 and an inert fluid cannula 54 are integral with stopper support 32 and are penetrating elastomer stopper 50 which is the closure for vacuum blood collection tube 68. Face seal assembly 40 is comprised of a face seal 56 containing holes 55 and 57 which are sealed to a face seal holder 58 by O-rings 60 and 62 thus providing communication with the interior of vacuum blood collection tube assembly 12 through serum cannula 52, hole 55 and a serum conduit 64 and also through inert fluid cannula 54, an annular groove 33, hole 57, and an inert fluid conduit 66.

Referring to FIG. 3 rotation of vacuum blood collection tube assembly 12 about its longitudinal axis has caused higher density formed elements 74 to be centrifuged against vacuum blood collection tube 68 with lower density serum 72 layered on top of formed elements 74. Residual air 70 inside the vacuum blood collection tube assembly 12 occupies the location nearest the axis of rotation due to its extremely low density.

Referring to FIG. 4 a high density inert fluid 76, introduced via inert fluid cannula 54, is against the inner wall of vacuum blood collection tube 68. Too obtain this condition the inert fluid density must be higher than the density of the formed elements or higher than about 1.09 gram/cubic centimeter. When the density of the inert fluid is greater than the density of serum but less than the density of formed elements partitioning of serum from formed elements still occurs but the positions of inert fluid 76 and formed elements 74 in FIG. 4 would be exchanged. Inert fluid 76 should dissolve very little of the analyte chemicals in serum 72 to avoid altering the concentration of analytes in serum 76. The analytes are generally water soluble so inert fluid 76 must have a low solubility of water in it. Also inert fluid 76 must have a high purity to avoid altering serum 72 and should have a boiling point high enough to avoid boiling problems. A suitable inert fluid 76 is a perfluorocarbon liquid such as FC-70 Fluorinert manufactured by 3M Company. At 25C this liquid has a density of 1.94 gram/cubic centimeter, boiling point of 275C, surface tension of 18 dyne/centimeter, and solubility of water of 8 parts per million. FC-70 Fluorinert may be too expensive. Lower cost liquids which may be satisfactory are trichloroethylene, tetrachloroethylene, n-butyl phthalate, Dow Corning phenylmethylpolysiloxane oils DC560 and DC710, Dow Corning fluorosilicone oil FS1265. Going back to FIG. 4 formed elements 74 and serum 72 are displaced radially inwards by inert fluid 76 and serum 72 is brought into contact with serum cannula 52.

Referring to FIG. 5 inert fluid 76 in an inert fluid reservoir 78 is in communication with an inlet of a pump 80 which is a reversible positive displacement pump such as a peristaltic tubing pump, The outlet of pump 80 is in communication with an inert fluid conduit 66 and a pressure switch 88 which is connected to an electronic control 90 which regulates pump 80. A contaminant detector 82 is inserted in serum conduit 64 and is connected to actuate a 3 way valve 92 which connects serum conduit 64 either to a serum delivery conduit 93 or to a waste reservoir 94. 3 way valve 92 is a zero dead volume type to minimize loss of serum. Serum delivery conduit 93 is positioned with its delivery end over a serum receptacle 86. Serum 72 in serum receptacle 86 is then presented to a serum analyzer by conventional means (not shown) for analysis.

Referring to FIG. 6 item 96 is a washing tube which has replaced vacuum blood collection tube, assembly 12 by rotation of carousel 51. A washing fluid reservoir 102 communicates with the inlet of a pump 104 connected to a timer 106. The outlet of pump 104 is in communication with a cavity inside washing tube 96. A conventional source of compressed air (not shown) 110 communicates with the same cavity inside washing tube 96 via a normally closed valve 108 connected to timer 106. An O-ring 98 is between washing tube 96 and stopper support 32. The bottom of the cavity in washing tube 96 communicates with waste reservoir 94 via a normally closed valve 112 connected to timer 106.

Referring to FIG. 7 a tungsten filament lamp 116 has a lens 118 which focuses a beam of light through a band pass filter 120 centered at 530 nanometers and through a beam splitter 122 and through an aperture 124 and through a transparent flow cell 114 containing serum 72 and through an aperture 126 to silicon PIN photodiode 128 connected to an operational amplifier 130 with a feedback potentiometer 132. Some light from beam splitter 122 passes through an aperture 134 to a silicon PIN photodiode 136 connected to an operational amplifier 138 with a feedback resistor 140. Resistors 142, 144, and 148 are connected to an operational amplifier 146. A threshold setting potentiometer 152 is connected to a fixed positive voltage and also to a conventional pulse duration and time delay circuitry 150 (details not shown) which in turn is connected to an electric actuator 154 mechanically connected to 3 way valve 92.

Referring to FIG. 8 a machine readable marking 156, such as a bar code label, is affixed to a vacuum blood collection tube assembly 12 and aligned with an optical identification sensor 158, such as a bar code reader.

Operation

General Operation A vacuum blood collection tube assembly containing clotted blood is rotated about its longitudinal axis at a speed in the order of 10,000 to 20,000 RPM for a time sufficient for separation of serum from the formed elements. While still rotating an inert fluid of high density, immiscible with the blood phases, is introduced into the vacuum blood collection tube assembly which displaces the serum radially inwards towards the axis of rotation due to centrifugal forces. A cannula on the axis of rotation permits the escape of first the air and secondly the serum itself through a delivery conduit to a serum receptacle. A contaminant detector in the serum delivery conduit senses the presence of air, microclots, cellular aggregates, and fibrin strands and diverts them to a waste reservoir thus delivering only clean serum to the serum receptacle for analysis.

After delivery of serum the vacuum blood collection tube assembly is replaced by a washing tube and the serum receptacle is replaced by a waste reservoir by conventional means (not shown). Then wash fluid is pumped through the serum conduits to expel serum followed by dry compressed air to expel wash fluid and dry the serum conduits. The system is now ready to process another blood sample following return to a vacuum blood collection tube assembly and a serum receptacle. A bar code label on the outside of each vacuum blood collection tube assembly and a bar code reader provide identification of each blood blood sample while each vacuum blood collection tube assembly is rotating. Specific Operation:A number of vacuum blood collection tube assemblies 12 are loaded manually into a rotary carousel 51 which aligns them one at a time with a tube support 14 and a stopper support 32. A pressurized fluid, such as compressed air, is applied to a port 30 of a cylinder 20 while a port 28 is exposed to a lower pressure. A piston 18 rises and lifts a bearing 16, a tube support 14, and a vacuum blood collection tube assembly 12, which is then no longer supported by carousel 51, but is lifted into engagement with a stopper support 32 which results in cannulae 52 and 54 penetrating through a stopper 50. A motor 46 is energized which rotates stopper support 32 and vacuum blood collect ion tube assembly 12 via a pulley 44 and a drive belt 42. Stopper support 32 rotates inside bearings 34 and 36 supported in a stationary support structure 38.

The blood sample inside vacuum blood collection tube assembly 12 is thus subjected to centrifugal forces in the order of 1000 g's. Formed elements 74 consisting of red and white blood cells enmeshed in a network of fibrin strands are forced to the inner diameter of vacuum blood collection tube 68 as shown on FIG. 3. This is due to the formed elements having a density in the order of 1.09 gram/cubic centimeter and the serum having a density in the order of 1.03 gram/cubic centimeter. Air 70 with a density in the order of 0.001 gram/cubic centimeter thus occupies the inner cylindrical volume inside the vacuum blood collection tube assembly 12. Air 70 is at atmospheric pressure due to venting to ambient air via serum cannula 52, contaminant detector 82, 3 way valve 92, and a serum delivery conduit 93.

An inert fluid is now pumped from an inert fluid reservoir 78 by a pump 80 through an inert fluid conduit 66, a hole 57, an annular groove 33, and an inert fluid cannula 64 into the rotating vacuum blood collection tube assembly 12. Inert fluid 76 inside vacuum blood collection tube assembly 12 moves to the position shown on FIG. 4 and displaces the formed elements 74, and and serum 72 radially inwards. Continued pumping of inert fluid 76 into the vacuum blood collection tube assembly 12 causes expulsion of air 70 and then serum 72 out through serum cannula 52, a hole 55, a serum conduit 64, a contaminant detector 82, a 3 way valve 92, a serum delivery conduit 93 into serum receptacle 86. Serum 72 may then be presented to an automated serum chemistry analyzer for analysis.

In the event serum cannula 52 is obstructed by formed elements 74 the discharge pressure of pump 80 rises and actuates pressure switch 88 which, operating through an electronic control 90, stops pump 80, reverses pump 80 for a brief period of time in the order of one second, and then causes normal pumping to resume. Reversal of pump 80 expels material obstructing serum cannula 52 after which normal pumping can resume.

In the event contaminant is detected by the contaminant detector 82 3 way valve 92 is operated to divert the contaminant from serum delivery conduit 93 to a waste conduit 94. The operation of 3 way valve 92 is delayed from the time contaminant is first detected by contaminant detector 82 for a period of time slightly less than the time required for the contaminant to flow from contaminant detector 82 to 3 way valve 92. 3 way valve 92 is operated for a minimum period of time in the order of 0.1 second plus an additional period of time equal to the time that contaminant is being detected by contaminant detector 82. This timing prevents contaminant being delivered to the serum receptacle 86 while a small amount of serum preceding and following the contaminant is lost to waste reservoir 94.

Contaminant detector 82 is basically a dual beam calorimeter where one light beam is a sample beam and a second light beam is a reference beam. This allows for some light source degradation or changes in silicon photodetectors due to changes in ambient air temperature or other factors while preserving the accuracy of the calorimeter. The sensitivity of the contaminant detector is enhanced for detection of microclots and erythrocyte aggregates by the use of wavelenghts for both the sample and reference beams centered about 530 nanometers because the hemoglobin in microclots and erythrocyte aggregates absorbs light strongly at 530 nanometers. The sensitivity of the contaminant detector may thus be enhanced by the use of wavelengths which are most strongly absorbed by the contaminant.

Light from a tungsten filament lamp 116 is focused by a lens 118 into apertures 124 and 134 after being passed through a band filter 120 and a beam splitter 122. Light into aperture 134 forms the reference beam which is detected by a silicon PIN photodiode 136. The photon-induced current from silicon photodiode 136 is input to operational amplifier 138 configured with a feed-back resistor 140 to form a transimpedance amplifier whereby the current from silicon PIN photodiode 136 is converted into a proportional voltage at the output of operational amplifier 138.

Light passing through aperture 124 passes through flow cell 114 containing serum 72 and then through aperture 126 into silicon PIN photodiode 128. Aperture 126 prevents light scattered by the corners of flow cell 114 from reaching silicon PIN photodiode 128. The photon-induced current from silicon PIN photodiode 128 is input to an operational amplifier 130 configured with a feedback potentiometer 132 to form a transimpedance amplifier. Potentiometer 132 is adjusted so the voltage outputs of operational amplifiers 130 and 138 are equal when flow cell 114 is full of normal serum 72 and no contaminant is present in flow cell 114. When contaminants such as air, clots, cellular aggregates, or fibrin strands are present in flow cell 114 some of the light passing through flow cell 114 is blocked. Then less current is sent by silicon PIN. photodiode 128 to operational amplifier 130 and the output voltage of operational amplifier 130 decreases.

Operational amplifier 146 is configured with resistors 142, 144, and 148 as a voltage difference amplifier. Thus when the output voltage of operational amplifier amplifier 130 becomes less than the output voltage of operational amplifier 138 the output voltage of operational amplifier 146 moves from zero in a positive direction.

This positive voltage from operational amplifier 146 is input to a conventional pulse duration and time delay circuitry 150 which compares this input voltage to a threshold voltage set by a potentiometer 152. When the threshold voltage from potentiometer 152 is exceeded by the output voltage from operational amplifier 146 then pulse duration and time delay circuitry 150 is triggered to produce a fixed output voltage which is delayed a fixed time and which has a duration equal to the time duration by which the input voltage exceeds the threshold voltage plus a fixed time duration in the order of 0.1 second. The output voltage of pulse duration and time delay circuitry circuitry 150 operates an electric actuator 154 which operates 3 way valve 92 to the position where the output flow from contaminant detector 82 is delivered to waste reservoir 94.

Pump 80 is operated for a predetermined perion of time to produce a predetermined volume of serum 72 in the serum receptacle 86. This predetermined period of time is the time it takes pump 80 to deliver the predetermined volume of serum 72 and also fill an empty conduit from contaminant detector 82 to delivery conduit 93. This predetermined time does not include the time 3 way valve 92 is positioned to deliver contaminant to waste reservoir 94.

Following delivery of a predetermined volume of serum 72 to serum receptacle 86 rotation of vacuum blood collection tube assembly 12 is stopped. Piston 18 is lowered by applying high pressure to port 28 and low pressure to port 30 of cylinder 20. Vacuum blood collection tube assembly 12 is pushed off serum cannula 52 and inert fluid cannula 54 and lowered onto support by carousel 51 by suitable conventional means (not show). Carousel 51 is then rotated by conventional means (not shown) so washing tube 96 is aligned with stopper support 32. Piston 18 is raised by applying high pressure to port 30 and low pressure to port 28 of cylinder 20. This causes washing tube 96 to be sealed to stopper support 32 by an O-ring 98. At the same time that carousel 51 is aligning washing tube 96 with stopper support 32 serum conduit 93 is moved so its exit end is over waste reservoir 94 by conventional means (not shown).

Compressed air 110 is admitted briefly to the central cavity of washing tube 96 through a normally closed valve 108 energized by a conventional timer 106. This air travels through serum cannula 52, hole 55, serum conduit 64, contaminant detector 82, 3 way valve 92, and serum delivery conduit 93 expelling serum therefrom. Next a washing fluid 100 from a washing fluid reservoir 102 is delivered by a pump 104 for a predetermined time controlled by a timer 106 into the central cavity of washing tube 96. Washing fluid 100 then passes through cannula 52, hole 55, serum conduit 64, contaminant detector 82, 3 way valve 92, and serum delivery conduit 95 thereby washing out most of the residual serum 72. Next compressed air 110 from a conventional source is admitted into the central cavity of washing tube 96 through a normally closed valve 108 energized by timer 106 for a predetermined period of time sufficient to expel substantially all of residual washing fluid 100 and then to Substantially dry the interiors of serum cannula 52, hole 55, serum conduit 64, contaminant detector 82, 3 way valve 92, and serum delivery conduit 93.

Initially, when compressed air 100 is introduced into the central cavity of washing tube 96, air bubbles will be formed which will rise to the surface of washing fluid 100 and burst. This will provide some washing of the external surfaces of cannulae 52 and 54. Shortly after energizing normally closed valve 108 to expel washing fluid 100 from the aforementioned conduits a normally closed valve 112 is energized by timer 106 for a predetermined period of time sufficient to substantially empty washing tube 96 of washing fluid 100.

Inert fluid cannula 54 will normally be filled with inert fluid 76. Any serum 72 or washing fluid 100 which may be present inside the open end of inert fluid cannula 54 just prior to expulsion of washing fluid 100 from washing tube 96 may be expelled by operating pump 80 briefly to discharge a small volume of inert fluid 76 from inert fluid cannula 54 thereby purging inert fluid cannula 54 of any residual serum 72 or washing fluid 100.

At any time vacuum blood collection tube assembly 12 is rotating a machine readable marking 156 may be scanned by an optical identification sensor 158 to provide sample identification information to an automated serum analyzer.

This method for obtaining clean, uncontaminated serum from an unopened vacuum blood collection tube assembly may also be used to obtain clean, uncontaminated plasma when the blood sample is anticoagulated. Operated is unchanged. The foregoing descriptions apply except that the word "plasma" replaces the word "serum" and the words "formed elements" replace the word "clot". Summary, Ramifications, and Scope Accordingly, the reader will see that the method herein described provides for the removal of serum or plasma from a blood sample contained in an unopened vacuum blood collection tube assembly. Furthermore, this method provides the following advantages over methods of the existing art:

it provides easy automation of the entire process of partitioning a blood sample and delivering a particular phase to a remote receiver vessel without manual intervention it avoids biohazardous conditions by not opening vacuum blood collection tube assemblies it avoids biohazardous conditions by not requiring manual handling of blood or its components it reduces the cost for this process by not requiring manual intervention it reduces the cost for this process by the use of a standard, unmodified vacuum blood collection tube assembly it reduces the cost for this process by not requiring additional apparatus or devices for removal and dispensing of the removed blood phase following centrifugal partitioning of the blood phases it provides for the removal from a removed blood phase of contaminants such as air, microclots, cellular aggregates, or fibrin strands which can cause malfunction of serum or plasma analyzers it provides for the accurate and precise delivery of a volume of a removed phase to a receiver vessel Although the description above contains many specificities, these should not be construed as limiting the scope of the invention but as merely providing illustrations of some of the presently preferred embodiments of this invention. For example, the vacuum blood collection tube assembly can be rotated about other than a vertical axis and by means other than an electric motor and a drive belt such as by air or by gears or by means integral with the tube support. The air operated piston and cylinder used to lift the vacuum blood collection tube aaembly could be operated by an hydraulic fluid or be replaced by an electrical linear actuator means. The optical contaminant detector could be replaced by an electrical detector sensing the change in impedance in a conduit caused by the presence of contaminant.

The method is applicable when plasma or other blood components are to be removed from an unopened vacuum blood collection tube assembly or when materials other then blood components are to be separated and removed from a closed cylindrical chamber.

The operations of washing and drying the conduits carrying a removed blood component may be omitted when carryover from one sample to the newt sample is not important, Similarly, the operations of detecting the presence of contaminant in the removed component and removing the contaminant by diverting it to a waste container may be omitted when such contaminant removal is not required. Metering of the volume of the removed component may be omitted when such metering is not important.

Thus the scope of the invention should be determined by the appended claims and their legal equivalents, rather than by the examples given.

I claim:

1. A method of removing contaminants from a flowing liquid phase comprising the steps of:
   (a) passing said liquid phase through a contaminant detector means, and
   (b) passing said liquid phase emerging from said contaminant detector means through a diverter means, and
   (c) operating said diverter means to divert said liquid phase emerging from said contaminant detector means to a waste vessel when contaminant is first detected by said contaminant detector means and continuing to divert said liquid phase for a predetermined period of time thereafter, and then
   (d) returning to non-diverted flow of said liquid phase, whereby contaminants in said flowing liquid phase are removed therefrom.

2. A method as described in claim 1 wherein said contaminant detector means employs optical sensing means, further including the steps of:
   (a) passing said liquid phase through a transparent conduit, and
   (b) directing a light beam through said transparent conduit, and
   (c) producing an electrical signal proportional to the intensity of said light beam incident to said transparent conduit, and
   (d) producing an electrical signal proportional to the intensity of said light beam emerging from said transparent conduit, and
   (e) amplifying said electrical signals from said incident and said emerging light beams so both said amplified signals are substantially equal when said transparent conduit is full of said liquid phase and no contaminants are present within said transparent conduit in the path of said incident light beam, and (f) comparing said amplified signals and producing an output signal whenever said amplified transmitted light beam signal is less than said amplified incident light beam signal by a predetermined amount, and (g) causing said output signal to operate said diverter means to direct said liquid phase to said waste vessel, and (h) maintaining diversion of said liquid phase to said waste vessel for a time period equal to a predetermined period of time plus a period of time equal to that time period during which said contaminant is detected, whereby said contaminant is removed from said liquid phase being delivered to said waste vessel.

3. A method as described in claim 2 wherein said light beam is restricted to a limited band of wavelengths, whereby the sensitivity of said contaminant detector is enhanced by the use of wavelengths strongly absorbed by the contaminant.

4. A method as described in claim 3 wherein said light beam is less than approximately 100 nanometers wide at its 50% intensity wavelengths and is centered about approximately 530 nanometers, whereby absorption of said incident light beam by the hemoglobin in microclots and erythrocyte aggregates is increased, and their detection is enhanced.

5. method as described in claim 1 wherein said contaminants detected and removed from said liquid phase are air, microclots, cellular aggregates, and fibrin strands.

6. A method as described in claim 1 further including the step of providing a predetermined time delay between initial detection of said contaminant by said contaminant detector means and operation of said diverter means, thereby allowing time for said contaminant to travel from said contaminant detector means to said diverter means, whereby the loss of said liquid phase to said waste vessel is reduced.

7. A method as described in claim 1 wherein said diverter means is an electrically operated, zero dead volume, 3 way valve.

* * * * *